(12) United States Patent
Bajic et al.

(10) Patent No.: US 10,466,213 B2
(45) Date of Patent: Nov. 5, 2019

(54) SECONDARY ULTRASONIC NEBULISATION (71) Applicant: Micromass UK Limited, Wilmslow (GB)

(72) Inventors: Stevan Bajic, Sale (GB); David S Douce, Congleton (GB); Gordon A Jones, Buxton (GB)

(73) Assignee: MICROMASS UK LIMITED, Wilmslow (GB)

( * ) Notice: Subject to any disclaimer, the term of this patent is extended or adjusted under 35 U.S.C. 154(b) by 288 days.

(21) Appl. No.: 15/387,133

(22) Filed: Dec. 21, 2016

(65) Prior Publication Data
US 2017/0176401 A1   Jun. 22, 2017

(30) Foreign Application Priority Data
Dec. 22, 2015   (GB) .................................. 1522594.9

(51) Int. Cl.
| | | |
|---|---|---|
| *G01N 30/72* | (2006.01) | |
| *H01J 49/04* | (2006.01) | |
| *B05B 17/06* | (2006.01) | |
| *G01N 30/06* | (2006.01) | |
| *G01N 30/84* | (2006.01) | |

(52) U.S. Cl.
CPC ....... *G01N 30/724* (2013.01); *B05B 17/0607* (2013.01); *B05B 17/0623* (2013.01); *G01N 30/06* (2013.01); *H01J 49/045* (2013.01); *H01J 49/0445* (2013.01); *H01J 49/0454* (2013.01); *G01N 2030/8447* (2013.01); *G01N 2030/8452* (2013.01); *G01N 2030/8458* (2013.01)

(58) Field of Classification Search
CPC ......... G01N 30/724; G01N 2030/8447; G01N 2030/8452; G01N 2030/8458; H01J 49/0445; H01J 49/0454; B05B 17/0607
See application file for complete search history.

(56) References Cited

U.S. PATENT DOCUMENTS

| | | | |
|---|---|---|---|
| 4,582,654 A * | 4/1986 | Karnicky | ............ B05B 17/0607 239/102.2 |
| 7,989,763 B2 | 8/2011 | Fedorov et al. | |
| 8,153,964 B2 | 4/2012 | Chen et al. | |
| 8,202,494 B2 | 6/2012 | Li et al. | |
| 8,232,520 B2 | 7/2012 | Cristoni | |
| 8,415,619 B2 | 4/2013 | Goodlett et al. | |
| 9,190,257 B2 * | 11/2015 | Otsuka | .................. H01J 49/165 |
| 9,506,852 B2 | 11/2016 | Hentz et al. | |
| 2014/0083174 A1 | 3/2014 | Rebound et al. | |

FOREIGN PATENT DOCUMENTS

| | | |
|---|---|---|
| GB | 2507297 | 4/2014 |
| JP | S59210358 | 11/1984 |
| JP | 2009/008689 | 1/2009 |

* cited by examiner

*Primary Examiner* — Paul M. West
(74) *Attorney, Agent, or Firm* — Womble Bond Dickinson (US) LLP; Deborah M. Vernon; Heath T. Misley

(57) ABSTRACT

A secondary ultrasonic nebulization device is disclosed comprising: a liquid sample delivery capillary; a sample receiving surface arranged for receiving a liquid sample from the capillary; and an ultrasonic transducer configured for oscillating the surface so as to nebulize the liquid sample received thereon, wherein the device is configured such that the oscillations of the surface by the ultrasonic transducer cause charged droplets and/or gas phase ions to be generated from the sample.

19 Claims, 5 Drawing Sheets

SECONDARY ULTRASONIC NEBULISATION

CROSS-REFERENCE TO RELATED APPLICATION

This application claims priority from and the benefit of United Kingdom patent application No. 1522594.9 filed on 22 Dec. 2015. The entire contents of this application are incorporated herein by reference.

FIELD OF THE INVENTION

The present invention relates generally to mass spectrometers and in particular to mass spectrometers in which an liquid analyte is nebulised and ionised prior to mass analysis.

BACKGROUND

Atmospheric Pressure Ionisation/mass spectrometry (API/MS) sources are known to utilise primary ultrasonic nebulisers that convert a flow of liquid into a charged aerosol. In these primary ultrasonic nebulisers the liquid flow passes directly through an electrospray nozzle which is ultrasonically agitated via a piezoelectric transducer.

Secondary ultrasonic nebulisers are also known in which a liquid sample is directed from one device to a spatially separated, ultrasonically-vibrated surface. For example, ultrasonic sample delivery systems are also known in which an ultrasonic transducer is arranged at the bottom of a liquid well for producing a burst of droplets, or a single droplet, for analysis. However, such systems have limited applications. For example, some of these systems are not compatible with continuous flow sample sources.

The present invention provides an improved ultrasonic nebulisation device, an improved spectrometer and improved methods of using the same.

SUMMARY

The present invention provides a secondary ultrasonic nebulisation device comprising:

a liquid chromatography separation device for separating a liquid sample;

a liquid sample delivery capillary forming part of, or arranged to receive, the liquid sample from the separation device;

a sample receiving surface arranged for receiving the liquid sample from the capillary; and an ultrasonic transducer configured for oscillating the surface so as to nebulise the liquid sample received thereon, wherein the device is configured such that the oscillations of the surface by the ultrasonic transducer cause charged droplets and/or gas phase ions to be generated from the sample.

The ultrasonic transducer according to the embodiments of the present invention provides a convenient mechanism for ionising or charging liquid chromatography eluent, without necessarily applying high voltages to the eluent. The sample may therefore be continually received at the oscillating surface, so as to preserve the chromatographic integrity of the sample, and ionised or charged by the oscillation of the surface.

US 2010/0301199 discloses a method of ionising analyte in a liquid sample by dropping a micro-liter droplet of the sample onto an ultrasonic transducer. However, US'199 does not recognise that an ultrasonic transducer can conveniently be used as a mechanism for ionising or charging eluent from a liquid chromatography device. The device in US'199 would not be capable of operating at the sample flow rates that would be received from chromatography devices. As such, the ionisation device of US'199 cannot continuously receive and ionise a sample and hence cannot preserve the chromatographic separation of components in a sample.

US 2012/0145890 discloses nebulising a liquid sample droplet using a surface acoustic wave. However, this nebulisation technique would not be used with liquid chromatography devices as it would also not be capable of operating at the sample flow rates that would be received from chromatography devices.

GB 2507297 discloses an impactor spray ion source that ionises a sample by nebulising it and directing the resulting droplets to impact on a target. The target may be vibrated with a piezoelectric device so as to assist in desolvation and reducing the size of the secondary droplets. However, unlike the present invention, GB'297 does not nebulise a liquid stream by receiving the liquid stream at an oscillating surface. Rather, the sample is already nebulised upstream of the target surface in GB297.

EP 1855306 discloses a similar device to GB'297, wherein the sample is nebulised before a target surface.

Embodiments of the present invention nebulise the sample using the mechanical oscillations of the sample receiving surface, and optionally not by surface acoustic waves (e.g. not by surface acoustic waves generated by electrodes). For example, embodiments of the present invention nebulise the sample using the mechanical oscillations formed by a piezoelectric transducer, and optionally amplified by an ultrasonic horn.

The chromatography separation device may be an HPLC device, a UPLC device or a convergence chromatography device.

The sample comprises analyte and the ultrasonic transducer oscillates the sample receiving surface so that the liquid sample thereon is nebulised so as to form analyte ions in gas phase and/or charged droplets of the analyte or sample solution. The nebuliser may therefore form a charged aerosol.

The purpose of the transducer in known secondary ultrasonic nebulisation devices has only been used to nebulise the sample received thereon, and not to form charged droplets of the sample/analyte and/or gas phase ions. In such known devices, the nebulised droplets may be electrically charged by applying a high voltage to the device, or the nebulised droplets may be ionised by a downstream ionisation device. In contrast, the ultrasonic transducer of the embodiments of the present invention is desired and configured to oscillate the sample receiving surface such that the oscillations of the surface cause the charged droplets and/or gas phase ions to be generated.

The nebulisation device may comprise a fluid injection system for injecting a fluid into the liquid sample downstream of the sample separation device for increasing the flow rate out of the capillary outlet.

An exit orifice of the capillary may be spaced at a distance from said sample receiving surface such that the liquid sample deposited on the sample receiving surface by the capillary remains in contact with the exit end of the capillary to form a liquid junction between the end of the capillary and the sample receiving surface. This enables a greater range of capillary flow rates to be used, since the liquid junction prevents the occurrence of intermittent dripping of the liquid sample onto the sample surface, which might otherwise occur at lower flow rates. Such intermittent dripping may be undesirable as it may result in an intermittent ion signal being generated.

The exit orifice of the capillary may be spaced a distance y from an area on the sample receiving surface on which the sample is deposited by the capillary, wherein y is selected from the group consisting of: ≤15 mm; ≤12.5 mm; ≤10 mm; ≤9 mm; ≤8 mm; ≤7 mm; ≤6 mm; ≤5.0 mm; ≤4.0 mm; ≤3.0 mm; ≤2.0 mm; ≤1.5 mm; ≤1.0 mm; ≤0.9 mm; ≤0.8 mm; ≤0.7 mm; ≤0.6 mm; ≤0.5 mm; ≤0.4 mm; ≤0.3 mm; ≤0.2 mm; and ≤0.1 mm.

The spacing between the exit orifice of the capillary and the sample receiving surface may be selected such that the sample receiving surface does not contact and/or seal the exit orifice of the capillary whilst the sample receiving surface is oscillated by the ultrasonic transducer.

Alternatively, the exit end of the capillary may contact the sample receiving surface during at least some of the time that the surface is oscillated by the ultrasonic transducer. The angle of the axis through the exit orifice relative to the sample receiving surface may be selected such that the sample receiving surface does not seal the exit orifice of the capillary whilst the sample receiving surface is oscillated by the ultrasonic transducer. For example, the angle may be ≤α degrees, wherein α is selected from the group consisting of: 40; 35; 30; 25; 20; 15; 10; and 5.

Alternatively, the exit orifice of the capillary may be spaced apart from the sample receiving surface and the nebulisation device may comprise a pump for pumping the liquid sample through the capillary at a rate such that a column or jet of liquid sample is ejected from the capillary and continuously provided to the sample surface. In this arrangement the exit orifice of the capillary is arranged a distance y from the area on the sample surface on which the sample is deposited by the capillary such that a liquid junction is not formed between the exit end of the capillary and the sample receiving surface.

The nebulisation device described herein may comprise a pump for pumping the liquid sample such that the liquid sample flows through said capillary at a rate selected from the group consisting of: ≥5 µL/min; ≥10 µL/min; ≥15 µL/min; ≥20 µL/min; 30 µL/min; ≥40 µL/min; ≥50 µL mL/min; ≥0.1 mL/min; ≥0.2 mL/min; ≥0.3 mL/min; ≥0.4 mL/min; ≥0.5 mL/min; ≥0.6 mL/min; ≥0.7 mL/min; ≥0.8 mL/min; ≥0.9 mL/min; ≥ and 1.0 mL/min. Alternatively, or additionally, to the pump rates described above, the pumping of the liquid sample may be such that the liquid sample flows through said capillary at a rate selected from the group consisting of: ≤5 µL/min; ≤10 µL/min; ≤15 µL/min; ≤20 L/min; ≤30 µL/min; ≤40 µL/min; ≤50 µL mL/min; ≤0.1 mL/min; ≤0.2 mL/min; ≤0.3 mL/min; ≤0.4 mL/min; ≤0.5 mL/min; ≤0.6 mL/min; ≤0.7 mL/min; ≤0.8 mL/min; ≤0.9 mL/min; and ≤1.0 mL/min.

When a continuous column or jet of sample solution is provided, the column or jet may have a velocity selected from the group consisting of: ≥0.5 m/s; ≥0.6 m/s; ≥0.7 m/s; ≥0.8 m/s; ≥0.9 m/s; ≥1.0 m/s; ≥1.1 m/s; ≥1.2 m/s; ≥1.3 m/s; ≥1.4 m/s; and ≥1.5 m/s.

The nebulisation device may comprise a pump for pumping the liquid sample through the capillary to the sample receiving surface, wherein the pump rate of the pump and the oscillation frequency of the sample receiving surface provided by the transducer are configured to operate at rates such that a wetted region or surface film of the liquid sample is continually arranged on said sample receiving surface.

Accordingly, the nebulisation device may comprise a pump system for pumping the liquid sample through the capillary; wherein the pump system is configured such that the rate at which the liquid sample is delivered to the sample receiving surface is equal to the average rate at which liquid sample is ejected from the sample surface by nebulisation. The nebulisation device may comprise a control system for varying the frequency at which the ultrasonic transducer oscillates the sample receiving surface; wherein the control system is linked to the pump system such that at any given frequency of oscillation for the surface, the rate at which the liquid sample is delivered to the sample receiving surface is maintained equal to the average rate at which liquid sample is ejected from the sample surface by nebulisation.

The sample receiving surface may be a substantially planar surface and the planar surface may be arranged at an angle to a longitudinal axis through the exit orifice of the capillary and/or at an angle to a longitudinal axis of the capillary. The angle may be an acute angle.

The longitudinal axis through the exit orifice and/or the longitudinal axis of the capillary may be substantially vertical or otherwise oriented so that the liquid sample drops onto the sample receiving surface under the effect of gravity.

The ultrasonic transducer may be coupled to the sample receiving surface such that the sample receiving surface is oscillated back and forth along an oscillation axis. The oscillation axis may be at an angle to the plane of the sample receiving surface for ejecting the sample droplets or ions away from the sample receiving surface with a velocity component along said oscillation axis and/or with a velocity component perpendicular to said oscillation axis. The angle may be an acute angle.

The sample receiving surface may be the longitudinal end of an elongated element that is mechanically coupled to the transducer.

The elongated element may be coupled to the transducer such that the transducer oscillates the elongated element along an oscillation axis that corresponds to the longitudinal axis of the elongated element. Alternatively, the oscillation axis may be angled or perpendicular to the longitudinal axis of the elongated element.

The elongated member forms an ultrasonic horn.

The elongated member may be a rod, such as a cylinder.

The sample receiving surface may be a surface formed by slicing through an elongated member, or by chamfering the end of an elongated member.

The nebulisation device may comprise a voltage supply arranged and configured to apply an electrical potential to at least one of: the sample receiving surface and/or said capillary and/or directly to the liquid sample for assisting in electrically charging the droplets and/or ions nebulised by the sample receiving surface. However, the application of ultrasonic power is believed to be more central to the ionisation process than applying an electrical potential. Accordingly, the nebuliser may be configured to nebulise and ionise the liquid sample without applying an electrical potential to the nebuliser or liquid sample.

The nebuliser described herein may be configured such that the cross-sectional area through which the fluid may flow at the exit end of the capillary is adjustable, and the nebulisation device optionally comprises a control device for adjusting said cross-sectional area, e.g. so as to adjust the flow rate/velocity through the capillary end for a given sample flow rate through the capillary.

The device may comprise a fluid blockage member arranged to be movable in and out of the exit end of the capillary in order to adjust said cross-sectional area at the exit end of the capillary. Alternatively, or additionally, the capillary and/or blocking member may be configured so that as the blocking member is moved along the axis of the capillary, said cross sectional area changes in size. This may be achieved by profiling the internal diameter of the exit end of the capillary to be tapered and/or profiling the outer diameter of the blocking member to be tapered.

The ultrasonic, transducer described herein may be a piezoelectric transducer.

The present invention also provides a mass or ion mobility spectrometer comprising:
a nebulisation device as described herein:
a vacuum chamber; and
an ion inlet orifice arranged between the sample receiving surface of the nebulisation device and the vacuum chamber for receiving said ions and/or charged droplets.

The nebulisation device may be configured such that the transducer oscillates the sample receiving surface such that said charged droplets and/or ions are nebulised from the surface with a velocity component towards the ion inlet orifice.

The nebulisation device may be configured such that the transducer oscillates the sample receiving surface along an oscillation axis, wherein the oscillation axis is at an angle to, or perpendicular to, an axis through the ion inlet orifice.

The sample receiving surface may at least partially face towards the ion inlet orifice.

The sample receiving surface may partially face upwards for receiving the liquid sample from the capillary.

The axis of the liquid capillary and/or the axis through the exit orifice of the capillary may be substantially orthogonal to both the oscillation axis and the axis through the ion inlet orifice.

The ion inlet orifice may be located a distance x from a part of the sample receiving surface on which the sample is deposited in use, wherein the distance x is selected from the group consisting of: ≤30 mm; ≤25 mm; ≤20 mm; ≤19 mm; ≤≤18 mm; ≤17 mm; ≤16 mm; ≤15 mm; ≤14 mm; ≤13 mm; ≤12 mm; ≤11 mm; ≤10 mm; ≤9 mm; ≤8 mm; ≤7 mm; ≤6 mm; and ≤5 mm.

When distance x is relatively small, ions and/or charged droplets that are generated by the nebuliser may be accelerated towards the ion inlet orifice under the influence of the high velocity gas flow that may exist between the region in which the nebuliser is located and the lower pressure of the vacuum chamber.

The ions and/or charged droplets may be urged towards the ion inlet orifice by an ion driving mechanism other than, or in addition to, the gas flow into the ion inlet orifice and vacuum chamber. For example, a gas evacuating port or cone may be arranged downstream of the nebuliser and a gas pump may be operable to draw gas downstream and through the evacuating port or cone. The port or cone may be arranged such that the gas flow therethrough urges the ions and/or charged droplets towards the ion sampling orifice. This may assist in urging the ions and/or charged droplets into the gas flow through the ion inlet orifice.

The ultrasonic transducer oscillates the sample receiving surface in use. However, the distance from said part of the sample receiving surface on which the sample is deposited to the ion inlet orifice may always remain within said distance x.

The spectrometer may be configured to maintain the vacuum chamber at a lower pressure than a nebulising region in which the sample receiving surface is located (e.g. by using a gas pump) so as to provide a gas flow from said nebulising region through the ion inlet orifice for drawing the ions and/or charged droplets through the ion inlet orifice.

The nebulising region may be maintained substantially at atmospheric pressure.

The spectrometer may comprise a heater for heating a structural component downstream of the sample receiving surface for heating the nebulised droplets and/or ions. The ion signal detected has been found to be dependent on the temperature of the downstream component.

The structural component may be the ion inlet orifice or another part of the ion inlet system. Alternatively, or additionally, a heated component may be arranged in the vacuum chamber downstream of the ion inlet orifice for heating the nebulised droplets and/or ions. The heated component for heating the nebulised droplets and/or ions is arranged in the flow path of the nebulised droplets and/or ions through the spectrometer, e.g. so that the droplets impact onto the heated component.

The heater may be configured to heat the structural component to a temperature selected from the group consisting of: ≥50° C.; ≥60° C.; ≥70° C.; ≥80° C.; ≥90° C.; ≥100° C.; ≥120° C.; ≥140° C.; ≥160° C.; ≥180° C.; ≥200° C.; ≥250° C.; ≥300° C.; ≥400° C.; ≥500° C.; ≥600° C.; ≥700° C.; ≥800° C.; ≥900° C.; and ≥1000° C.

The ultrasonic source signal intensity is found to be weakly dependent on the temperature of the gas in which the sample receiving surface is located and so the nebulisation device can operate satisfactorily at room temperature. Accordingly, the sample receiving surface may be located in a nebulising region that is maintained at room temperature.

The spectrometer comprises a mass analyser and/or ion mobility analyser for analysing ions generated or derived from the liquid sample.

The spectrometer may not comprise a plasma ionisation device for analysing the nebulised liquid solution and/or charged droplets and/or ions.

The present invention also provides a method of nebulising a liquid sample using a secondary ultrasonic nebulisation device comprising:
delivering a liquid sample from a liquid chromatography separation device to a sample receiving surface; and
ultrasonically oscillating the surface so as to nebulise the liquid sample, wherein said ultrasonically oscillating causes charged droplets and/or gas phase ions to be generated from the sample.

The method may use the nebuliser and its modes of operation described herein.

The method may comprise adding volatile additives into the liquid sample for assisting ionisation of analyte in the liquid sample during or after nebulisation at the sample receiving surface.

The additives may be activated so as to assist in said ionisation by ultrasonically oscillating the sample receiving surface; and/or the additives may be activated so as to assist in said ionisation by variations in pressure caused by ultrasonically oscillating the sample receiving surface.

The additives may undergo sublimation and display triboluminescence effects in order to assist in the ionisation.

The method may comprise operating the nebulisation device or spectrometer to perform any of the functionalities described herein.

The present invention also provides a method of mass spectrometry or ion mobility spectrometry comprising:
a method of nebulising a liquid sample as described herein; and
mass analysing or ion mobility analysing said gas phase ions, ions derived from said gas phase ions, or ions derived from said charged droplets.

The embodiments of the present invention provides an ion source for a wide range of polarities of analytes that can operate at low temperatures and without the need for high voltages.

Although the nebuliser has been described as comprising a liquid chromatography separation device for separating a liquid sample, it is contemplated that other sample separation devices may be used, or no sample separation devices used.

Accordingly, the present invention also provides a secondary ultrasonic nebulisation device comprising:

a liquid sample delivery capillary;

a sample receiving surface arranged for receiving a liquid sample from the capillary;

an ultrasonic transducer configured for oscillating the surface so as to nebulise the liquid sample received thereon, wherein the device is configured such that the oscillations of the surface by the ultrasonic transducer cause charged droplets and/or gas phase ions to be generated from the sample.

The present invention also provides a method of nebulising a liquid sample using a secondary ultrasonic nebulisation device comprising:

delivering a liquid sample to a sample receiving surface; and ultrasonically oscillating the surface so as to nebulise the liquid sample, wherein said ultrasonically oscillating causes charged droplets and/or gas phase ions to be generated from the sample.

The spectrometer disclosed herein may comprise one or more ion guides.

The spectrometer may comprise one or more ion mobility separation devices and/or one or more Field Asymmetric Ion Mobility Spectrometer devices.

The spectrometer may comprise one or more ion traps or one or more ion trapping regions.

The spectrometer may comprise one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("RD") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

The spectrometer may comprise a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) ion Cyclotron Resonance ("CR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser.

The spectrometer may comprise one or more energy analysers or electrostatic energy analysers.

The spectrometer may comprise one or more ion detectors.

The spectrometer may comprise one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter.

The spectrometer may comprise a device or ion gate for pulsing ions; and/or a device for converting a substantially continuous ion beam into a pulsed ion beam.

The spectrometer may comprise a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser.

The spectrometer may comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The spectrometer may comprise a chromatography or other separation device upstream of an ion source. The chromatography separation device may comprise a liquid chromatography or gas chromatography device. Alternatively, the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

Analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

Optionally, in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) C60 vapour or atoms; and (viii) magnesium vapour or atoms.

The multiply charged analyte cations or positively charged ions may comprise peptides, polypeptides, proteins or biomolecules.

Optionally, in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

A chromatography detector may be provided, wherein the chromatography detector comprises either: a destructive chromatography detector optionally selected from the group consisting of (i) a Flame Ionization Detector (FID); (ii) an aerosol-based detector or Nano Quantity Analyte Detector (NQAD); (iii) a Flame Photometric Detector (FPD); (iv) an Atomic-Emission Detector (AED); (v) a Nitrogen Phosphorus Detector (NPD); and (vi) an Evaporative Light Scattering Detector (ELSD); or a non-destructive chromatography detector optionally selected from the group consisting of: (i) a fixed or variable wavelength UV detector; (ii) a Thermal Conductivity Detector (TCD); (iii) a fluorescence detector; (iv) an Electron Capture Detector (ECD); (v) a conductivity monitor; (vi) a Photoionization Detector (PID); (vii) a Refractive Index Detector (RID); (viii) a radio flow detector; and (ix) a chiral detector.

The spectrometer may be operated in various modes of operation including a mass spectrometry ("MS") mode of operation; a tandem mass spectrometry ("MS/MS") mode of operation; a mode of operation in which parent or precursor ions are alternatively fragmented or reacted so as to produce fragment or product ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation a Quantification mode of operation or an Ion Mobility Spectrometry ("IMS") mode of operation.

BRIEF DESCRIPTION OF THE DRAWINGS

Various embodiments will now be described, by way of example only, and with reference to the accompanying drawings in which.

DETAILED DESCRIPTION

Atmospheric Pressure Ionisation/mass spectrometry (API/MS) sources have previously utilised ultrasonic nebulisers that convert a flow of liquid from a liquid chromatography (LC) column into a charged aerosol. These are primary ultrasonic nebulisers where the liquid flow passes directly through an electrospray nozzle which is ultrasonically agitated via a piezoelectric transducer.

In the secondary ultrasonic nebuliser described herein, the liquid flow is deposited onto a surface which, in turn, is ultrasonically agitated. In order to produce a stable aerosol from a secondary ultrasonic nebuliser, it is necessary to produce a wetted zone (finite volume reservoir, or film) on the transducer surface and to deliver a continuous, unperturbed liquid flow to the wetted zone. Liquid from a LC column can be fed to the transducer by positioning a capillary tube at some distance from the transducer and aiming the unbroken liquid jet to create a wetted zone on the vibrating surface. For example, for a 1:1 mixture of acetonitrile/water and a 130 µm internal diameter stainless steel tube at room temperature, a primary jet is formed at a flow rate of approximately ≥0.8 mL/min where the linear velocity of the liquid column is of the order 1 m/s. For liquid flow rates below this value, an intermittent, dripping flow may result which limits the practical flow rate range to wide bore analytical LC and UPLC columns. The onset of a stable liquid jet will depend on factors such as the internal diameter of the capillary, capillary material, liquid surface tension and temperature. In addition, the stability and directionality of the jet can be further influenced by factors such as capillary tip surface finish, cleanliness and induced charging from electric fields in the API source volume. All these factors impose limits on the amenability of secondary ultrasonic nebulisation to a wide range of chromatographic conditions.

An API source is disclosed herein that comprises a capillary tube that is very close to, or in contact with, a transducer surface such that it forms a stable liquid junction with the surface over a wide range of flow rates and mobile phase compositions.

Figure 1:
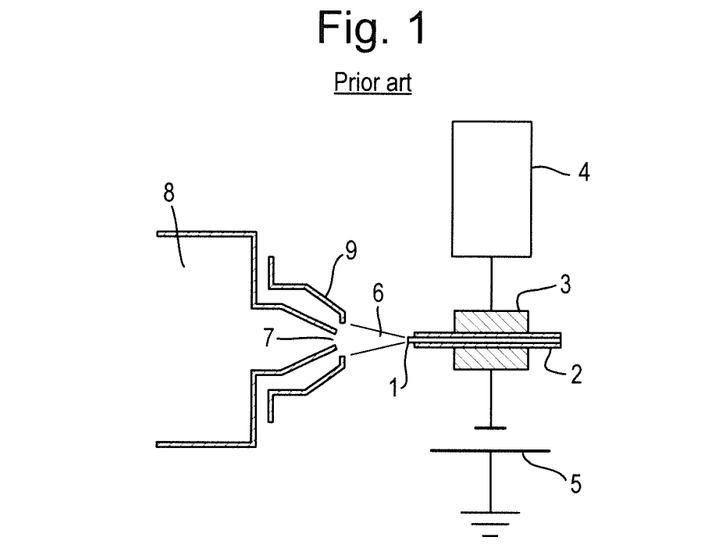
FIG. 1 shows a schematic of a prior art primary ultrasonic nebuliser.

FIG. 1 shows a schematic of a prior art primary ultrasonic nebuliser that is configured as an electrospray probe for an API source that provides ions for analysis by a mass spectrometer. Here, a liquid column 1 derived from the flow from a LC column is passed through a capillary 2 which is surrounded by an ultrasonic nozzle 3 that is in mechanical communication with the capillary 2. The nozzle 3 transmits ultrasonic energy from a transducer 4 to the capillary 2, which agitates the liquid column 1 to form a nebulised spray plume 6. In order to form charged droplets of predominantly one polarity, it is conventional to connect the capillary 2 to a high voltage power supply 5 which promotes double layer charge formation at the high electric field region where the liquid column 1 emerges from the capillary 2. Ions and charged droplets enter the mass spectrometer for analysis via an ion inlet orifice 7, which forms a boundary between the atmospheric pressure of the nebulised spray volume and the first vacuum region 8 of the mass spectrometer. A cone gas nozzle 9 is also shown that serves as a conduit for a flow of nitrogen gas that runs counter-current to the spray direction for aiding desolvation of charged droplets and reducing contamination of the inlet orifice 7.

Figure 2:
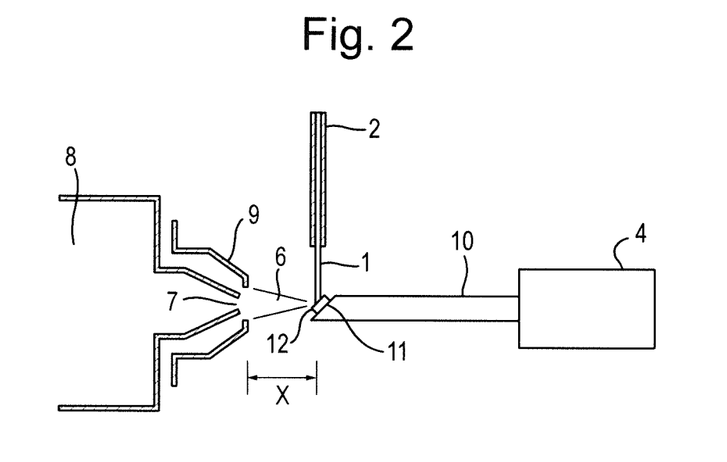
FIG. 2 shows a schematic of a secondary ultrasonic nebuliser according to an embodiment of the present invention wherein a jet or column of liquid sample is ejected from a capillary onto a sample receiving surface.

FIG. 2 is a schematic of an embodiment of the present invention which shows a secondary ultrasonic nebuliser that is configured as an API source for a mass spectrometer. Here, a flow of liquid from a LC column passes through a capillary 2 and forms a liquid column 1. The liquid column 1 is directed to impact on an ultrasonically agitated surface 11, which receives ultrasonic energy from a transducer 4 via a cylindrical transmitting horn 10. Experimental observations have revealed that the optimum conditions for spray stability and ion detection sensitivity occur when a wetted region or surface film 12 forms on the agitated surface 11. The size of the film 12 is exaggerated in FIG. 2 and is typically a few times greater than the width of the liquid column 1. The agitated surface 11 can receive a periodic displacement in either an axial or transverse direction, depending on the design of the ultrasonic system. The arrangement shown in FIG. 2 is best suited to oscillations along the longitudinal axis of the horn 10, where the force on the liquid reservoir 12 is normal to the agitated surface 11, thus leading to a nebulised spray plume 6 which has a significant velocity component in the X-direction towards the ion inlet orifice 7. Conversely, a transverse displacement (into and out of the page) would tend to disperse the liquid film 12 across the surface 11 resulting in the absence of a significant spray plume.

As shown and described in the arrangement of FIG. 1, it is possible to raise the electrical potential of the horn 10, and hence agitated surface 11, via connection to a high voltage power supply. A positive potential, for positive ion mass spectral analysis, can lead to ion signal enhancements. However, this effect is believed to be primarily due to a liquid column 1 steering effect in which a negatively induced voltage on the liquid column 1 results in its attraction towards the agitated surface 11 and more favourable conditions for a stable spray plume. The application of ultrasonic power is believed to be more central to the process of generating charged droplets than an applied voltage. Furthermore, it is important to position the agitated surface 11 such that the distance x between the film 12 on the agitated surface and the inlet orifice 7 is relatively small, e.g. x≤5 mm. When distance x is relatively small, ions and charged droplets that are generated are accelerated towards the ion inlet orifice 7 under the influence of the high velocity gas flow that exists between the atmospheric pressure of the source and the lower pressure of the first vacuum region 8.

The embodiment of FIG. 2 has been used as an API source for MS analysis at flow rates of, for example, 0.9 mL/min. Here, a stainless steel capillary 2 was used with an internal diameter of 130 µm and an outer diameter of 220 µm. The capillary 2 was positioned approximately 10 mm above surface 11. Surface 11 was formed by cutting a 45° chamfer on the end of a stainless steel rod having a length of 30 mm and a diameter of 1.6 mm. This rod was screwed into the cylindrical ultrasonic horn 10, which had a length of 90 mm and a diameter of 5 mm. The horn was driven by a 40 kHz transducer 4, which produced an axial displacement of 18 µm at the end of the horn 10.

When the LC flow rate is reduced to 0.3 mL/min, the liquid column 1 becomes unstable and exhibits a dripping flow which results in an intermittent MS signal. The onset of dripping is determined by the linear velocity of the liquid column 1 as it emerges at the end of the capillary 2. It can be shown that:

$$d = \left(\frac{4F}{\pi v}\right)^{1/2} \quad (i)$$

where d is the internal diameter of the capillary 2, F is the liquid flow rate and v is the velocity of the liquid column 1 at the end of the capillary 2.

As described above, it is found that typical LC solvents such as water, acetonitrile and methanol at room temperature will form a continuous jet for liquid column velocities in excess of around 1 m/s. According to equation (i) above, this condition is satisfied for a capillary 2 having an internal diameter d of 130 µm when the liquid flow rate F is 0.9 mL/min, but is not satisfied at a liquid flow rate F of 0.3 mL/min. In practice, a flow rate of 0.3 mL/min could be accommodated by the embodiment shown in FIG. 2, whilst forming a continuous jet, by reducing the internal diameter of the capillary 2 to around 80 µm. Alternatively, a flow rate of 0.3 mL/min could be accommodated by post-column addition (PCA) of an additional solvent flow between the LC column and the capillary 2 so as to boost the total liquid flow to 0.9 mL/min (for the capillary internal diameter of 130 µm). Both of these methods have been applied successfully at LC flow rates of 0.3 mL/min using the apparatus described in this paragraph. In fact, PCA of carefully chosen solvents can benefit MS sensitivity according to the particular chemistries of certain analytes.

From the above, it is apparent that a variation of this embodiment that utilises a dynamically adjustable capillary bore would provide an API source that could span a typical range of LC flow rates. The need to reduce the internal diameter of the capillary 2 in FIG. 2 poses some practical limitations at low flow rates (e.g. ≤0.1 mL/min) since small diameter capillaries are prone to blocking with real life samples and can form asymmetric jets due to poor handling or even modest tip contamination.

Figure 3A:
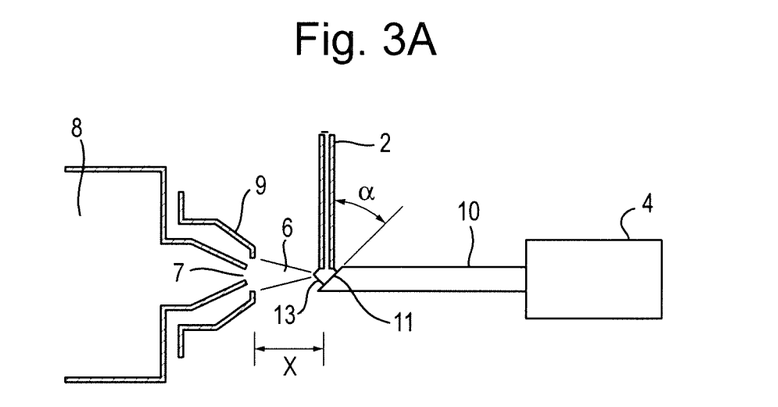
FIGS. 3A-3B show schematics of a secondary ultrasonic nebuliser according to other embodiments of the present invention wherein a liquid junction is formed between the capillary and sample receiving surface.
Figure 3B:
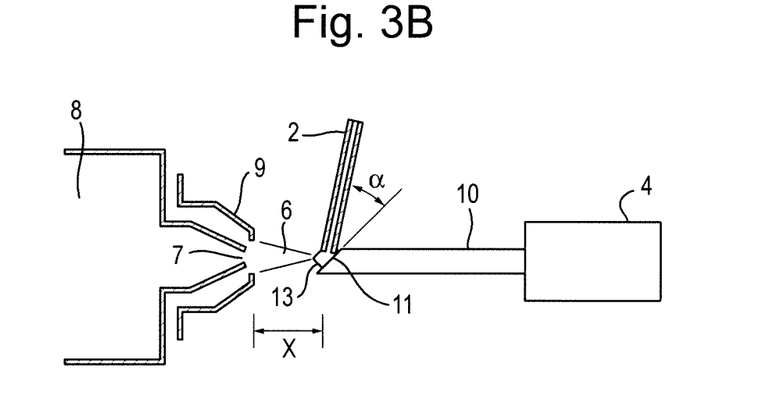

FIG. 3A is a schematic of another embodiment of the present invention. This embodiment uses the same components and operating parameters as that described in FIG. 2, but differs in that the capillary 2 is located in very close proximity to the ultrasonically agitated surface 11 such that it creates a liquid junction 13 between these two components. For example, the distance between the end of the capillary 2 and the surface 11 may be 0.1-0.5 mm. Depending on the orientation of the capillary 2 relative to the surface 11, care may need to be exercised to avoid contact between the end of the capillary 2 and the surface 11, which could mechanically deform the end of the capillary 2 and seal the bore of capillary 2 during agitation of the surface 11. Accordingly, it may be desired that the capillary 2 does not contact the surface 11 at all during agitation of the surface 11. This may be particularly desired when the angle α between the axis of the capillary 2 and the surface 11 is greater than a certain value, e.g. when α is ≥20°. However, in other embodiments in which the angle α is relatively low, e.g <20°, the end of the capillary 2 is less likely to be mechanically deformed to the extent that the bore will be sealed if the capillary 2 contacts with the surface 11. In these embodiments the end of the capillary may contact the surface 11 during agitation of the surface 11, and may even remain in contact with the surface 11 during agitation. Such an embodiment is shown in FIG. 3B. As in FIG. 3A, it can be seen that the embodiment of FIG. 3B also forms a liquid junction 13 between the capillary 2 and surface 11. Although the capillary blocking effect has been described to occur when the capillary 2 contacts the surface 11 with an angle α≥20°, it will be understood that the effect may still occur (to a different extent) at other angles.

The embodiments having a liquid junction 13 eliminate the flow rate dependency issues highlighted above. This liquid junction technique has been demonstrated to operate routinely as an API/MS source with a 40 kHz transducer, a capillary 2 having an internal diameter of 90 µm and for flow rates in the range from 0.1 to 0.8 mL/min. The peak-to-peak displacement of the ultrasonically oscillated surface 11 was approximately 18 µm.

The ultrasonic apparatus described in FIG. 3A has been compared to a conventional nitrogen-assisted ESI probe for the UPLC/IVIS analysis of a mixture of six analytes by multiple reaction monitoring (MRM) on a triple quadrupole mass spectrometer. In the ESI experiment, a cold nitrogen gas was used to aid nebulisation and a hot nitrogen gas flow was used to aid droplet desolvation. In the ultrasonic nebulisation experiment, a hot nitrogen gas flow (typically 250° C., not shown in FIGS. 3A-3B) was used to assist desolvation of the nebulised droplets. The following six analyte amounts were eluted into the API sources using a water/acetonitrile gradient at a flow rate of 0.6 hydroxyprogesterone (500 pg), sulphadimethoxine (10 pg), tolbutamide (1 ng), β-estradiol (1 ng), caffeine (20 pg) and δ-tocopherol (1 ng).

Figure 4A:
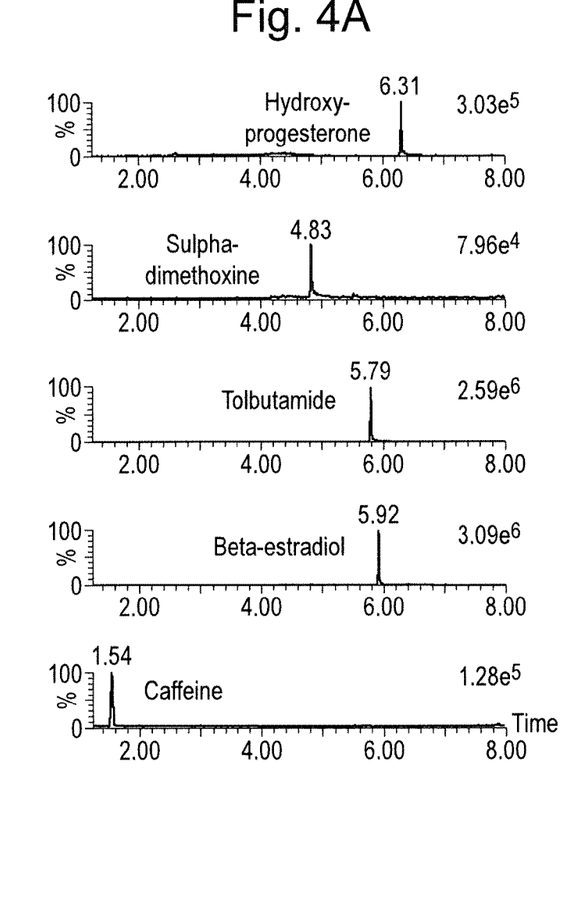
FIG. 4A shows chromatograms for five analytes obtained using a secondary nebuliser according to an embodiment of the present invention.
Figure 4B:
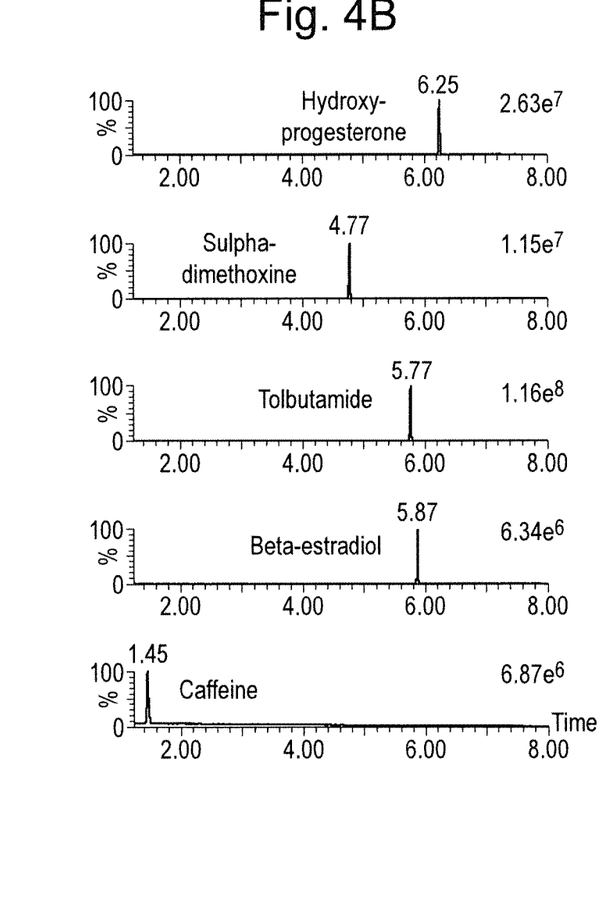
FIG. 4B shows chromatograms for the same five analytes obtained using a conventional ESI source.

FIG. 4A shows the UPLC/MS chromatograms obtained for five of the above six test analytes using the liquid-junction ultrasonic source, and FIG. 4B show the UPLC/MS chromatograms obtained for the same five test analytes using the conventional ESI source. From a comparison of the data, it is apparent that both sources produce equivalent peak half widths, which range from typically 1.0 to 2.2 seconds under these chromatographic conditions. The number in the upper right hand corner of each chromatogram represents the MS signal intensity obtained from each analyte in arbitrary units. These intensities suggest that the ESI source produces greater ion signals by factors of ×2 to ×144. However, if the signal-to-noise ratios for both source types are analysed, it is found that the performance is more comparable. Both sources give equivalent signal-to-noise ratios for caffeine and β-estradiol, whilst the signal-to-noise ratio obtained with the liquid-junction ultrasonic source can exceed that of ESI in the case of δ-tocopherol. Improvements in signal-to-noise are primarily due to a reduction in chemical noise background with the ultrasonic source, which could be advantageous for single quadrupole MS or other scanning MS systems.

Figure 5A:
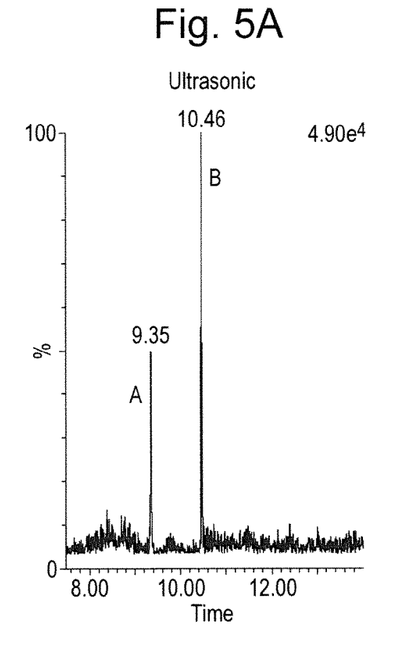
FIGS. 5A and 5B show chromatograms obtained for 6-tocopherol using a secondary nebuliser according to an embodiment of the present invention and a conventional ESI source, respectively.
Figure 5B:
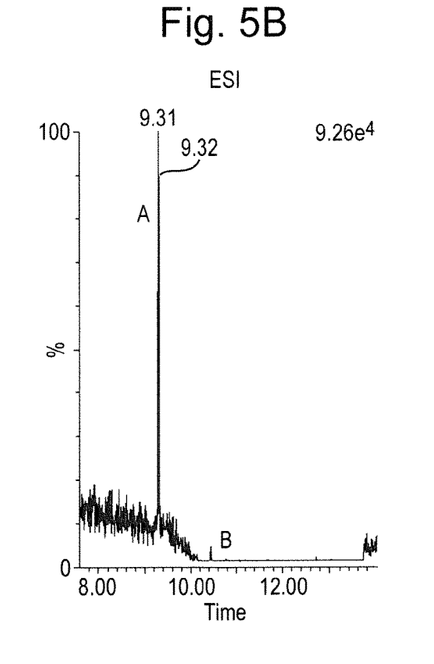
Figure 6:
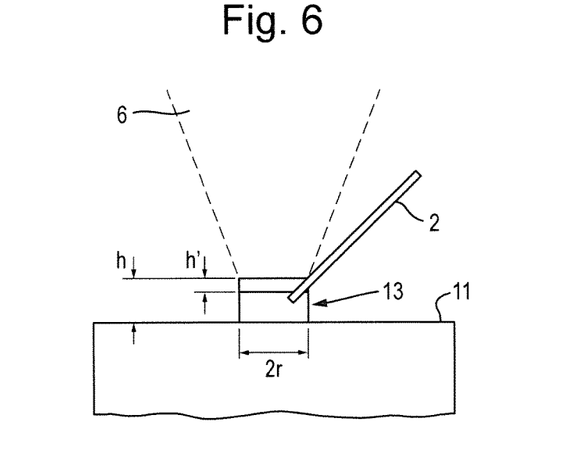
FIG. 6 shows a schematic of the liquid junction between the capillary and sample receiving surface in the embodiment of FIG. 3A.
Figure 7:
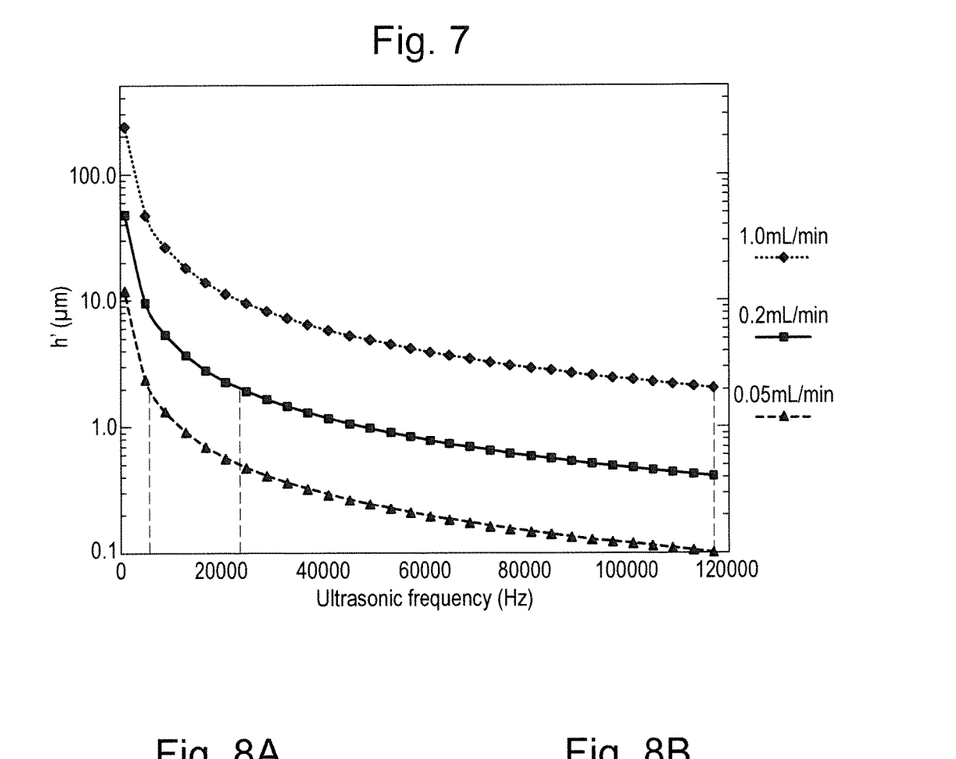
FIG. 7 shows the relationship between the amount of liquid added to the liquid junction of FIG. 6 and the ultrasonic transducer frequency that is required for nebulising this liquid, for various liquid flow rates through the capillary.

FIGS. 5A and 5B illustrate an additional advantage of the ultrasonic source over the ESI source, FIGS. 5A and 5B compare the chromatograms obtained for the least polar analyte of the above six analytes, δ-tocopherol, which elutes under very high organic (acetonitrile) conditions. The analyte δ-tocopherol is believed to produce a main peak ('B') at 10.46 mins, and a second peak ('A') at 9.35 mins which may be related or may be a contamination peak. As shown in FIG. 5A, the ultrasonic source produces strong peaks for both peaks A and B, whereas the ESI source shows only a very weak response for the main peak B. The weak ESI response can be correlated to a collapse in the total ion signal that occurs at approximately 10 mins in FIG. 5B, at which point the mobile phase composition reaches 100% acetonitrile. In comparison, as shown in FIG. 5A, the ultrasonic source is stable and produces a relatively flat baseline with no signal collapse under identical chromatographic conditions.

As described above, additional experiments have shown that further enhancement of the ultrasonic source performance can be obtained by PCA of appropriate solvents to the solution eluting from the chromatography column. For example, the analysis of δ-tocopherol may be enhanced by the PCA of water, whilst β-estradiol and tolbutamide may be enhanced by the PCA of acetonitrile.

The use of a hot nitrogen gas flow for intersecting the spray plume is critically important for the ESI source sensitivity at the chromatographic flow rates described herein. On the other hand, the ultrasonic source signal intensity is found to be very weakly dependent on the temperature of the gas and can operate satisfactorily at room temperature. However, the ultrasonic source is found to be strongly dependent on the temperature of the ion inlet system, i.e. the internal and external surfaces that constitute the source components 7, 8 and 9 in FIGS. 1-3. This temperature dependence is different for each analyte and can, for example, result in two orders of magnitude signal loss for acetaminophen as the inlet temperature is decreased from 150° C. to 80° C. This would suggest that gas phase ions can be formed downstream of the point of nebulisation. Sensitivity enhancements may therefore be achieved by heating a structural component of the spectrometer that is downstream of the agitated surface 11 so as to assist in ionising the nebulised analyte. For example, a heated bead or other obstruction may be arranged in the first vacuum region 8 such that droplets from the spray plume 6 impact onto the obstruction downstream of the ion inlet orifice 7. The obstruction may be heated to a temperature in the range 100-1000° C.

In the embodiments shown in FIGS. 2 and 3 it is important to create a stable surface film 12 or liquid junction 13 from which a spray plume 6 is ejected during the application of ultrasonic power. In order to maintain equilibrium, the volume of liquid entering the film 12 or junction 13 per periodic displacement cycle must be equal to the total volume of liquid ejected in the form of droplets from the film 12 or junction 13 per cycle.

FIG. 6 shows a close-up schematic of the liquid junction 13 of FIG. 3A, formed between the ultrasonically agitated surface 11 and the liquid capillary 2. It is arbitrarily assumed that the liquid junction 13 is in the form of a cylinder (exaggerated in size in the drawing) of radius r and maximum height h. The volume of liquid that is added to the liquid junction 13 prior to each ejection cycle is represented by a cylinder of radius r and height h'. Thus, in order to preserve equilibrium, greater liquid flow rates from the capillary 2 would require greater ultrasonic frequencies for the efficient ejection of liquid into plume 6. From the equilibrium conditions described above, it can be shown that the transducer frequency, f, will be given by:

$$f = \frac{F}{\pi r^2 n h'} \qquad \text{(ii)}$$

where F is the liquid flow rate through the capillary 2, r and h' are the radius and height respectively of the liquid cylinder added to the liquid junction 13 prior to each ejection cycle, and n is the number of ejections per cycle.

For axial ultrasonic oscillations, as described in the embodiments of FIGS. 2 and 3, n will be equal to one and liquid ejection will occur when the agitated surface 11 is at its closest approach to the inlet orifice 7.

FIG. 7 shows the relationship between the height h' of the liquid cylinder added to the liquid junction 13 prior to each ejection cycle and the transducer frequency f, for various liquid flow rates that are typically used in LC/MS applications. Here, the capillary tube bore diameter is 90 μm and it is assumed that the radius r of the liquid cylinder is 150 μm, i.e. approximately 3 times larger than the capillary tube bore diameter. By analogy with the impact of high Weber number water droplets on a metal surface, it is known that the initial droplet from the capillary 2 spreads along the surface 11 to form a thin film that is typically a few microns thick. At this thickness, the film becomes unstable and disintegrates to produce a number of secondary droplets, where the number of droplets is proportional to the droplet Weber number. If a similar thickness of instability is assumed for the upper portion of the liquid junction 13, i.e. say h'=2 μm, then FIG. 7 would suggest optimum transducer frequencies of 5000 Hz, 25000 Hz and 115000 Hz for LC flow rates of 0.05 mL/min, 0.2 mL/min and 1.0 mL/min, respectively. According to this model, it seems reasonable to assume that the 40 kHz fixed frequency used in this work was appropriate for the 0.6 mL/min flow rates of FIGS. 4 and 5. Furthermore, the ultrasonic source according to the present invention may incorporate a variable frequency transducer to optimise sensitivity and stability across the full spectrum of LC flow rates.

FIGS. 8A and 8B show plan views of embodiments of the present invention where the axes of the ultrasonic horn 10 and the inlet orifice 7 are perpendicular. Such arrangements are useful, for example, in API/MS sources in which it is not possible to align the axis of the ultrasonic horn 10 in the direction of the inlet orifice 7 due to access restraints, According to the embodiments of FIGS. 8A and 8B, the liquid capillary 2 (not shown) delivers an analyte solution to the surface 11 in the same way as described in the other embodiments so as to create a liquid film 12 or a liquid junction 13. The axis of the liquid capillary may be orthogonal to both the longitudinal axis of the transducer 10 and the axis through the ion inlet orifice 7 (e.g. the capillary 2 may be above and perpendicular to the page). The ultrasonically agitated surface 11 may be chamfered at 45° to the axis of the longitudinal horn 10 and the transducer 4 may oscillate the horn 10 along its longitudinal axis.

In the embodiment of FIG. 8A, the plane of the chamfered surface 11 is parallel to the axis through the ion inlet 7. As such, the axial ultrasonic displacement of the surface 11 results in a spray plume with main velocity components that are perpendicular to the axis through the ion inlet 7 (e.g.

portion 14 of the plume). This will generally lead to relatively low ion signals, although it will still function as an ion source, particularly when the surface 11 is relatively close to the ion inlet 7 (e.g. within a distance x≤5 mm).

Figure 8A:
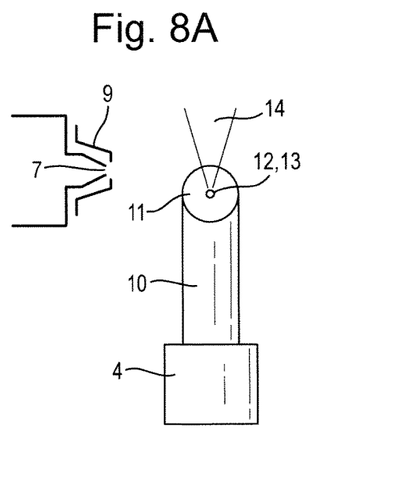
FIGS. 8A and 8B show schematics of secondary ultrasonic nebulisers according to further embodiments of the present invention, wherein the axes of the ultrasonic horn and the inlet orifice are perpendicular.
Figure 8B:
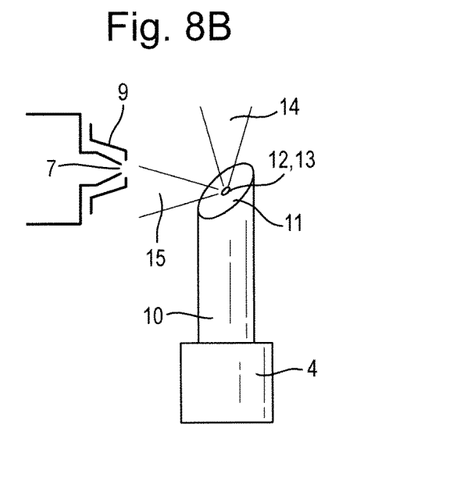

In the embodiment of FIG. 8B, the plane of the chamfered surface 11 partially faces towards the ion inlet 7 (i.e. the horn 10 is rotated 45° about its longitudinal axis relative to FIG. 8A). The axial ultrasonic displacement of the surface 11 results in a displacement force that is normal to the surface 11. This arrangement therefore results in a spray plume with greater velocity components directed towards the ion inlet 7 (e.g. portion 15 of the plume) and which significantly improves ion signal and hence source sensitivity.

It is known in the field of API sources that highly volatile additives, such as those used in Matrix-Assisted Inlet Ionisation (MAII) sources, can be added to LC solvents to promote ionisation. These additives typically undergo sublimation and display triboluminescence effects such as 3-nitrobenzonitrile. These additives may be used in embodiments of the present invention to enhance ionisation, for example, in regions of high shock such as that which exists at the ultrasonically agitated surface 11.

Although the present invention has been described with reference to various embodiments, it will be understood by those skilled in the art that various changes in form and detail may be made without departing from the scope of the invention as set forth in the accompanying claims.

The invention claimed is:

1. A secondary ultrasonic nebulisation device comprising:

a liquid chromatography separation device for separating a liquid sample;

a liquid sample delivery capillary forming part of, or arranged to receive, the liquid sample from the separation device;

a sample receiving surface arranged for receiving the liquid sample from the capillary;

an ultrasonic transducer configured for oscillating the surface so as to nebulise the liquid sample received thereon, wherein the device is configured such that the oscillations of the surface by the ultrasonic transducer cause charged droplets and/or gas phase ions to be generated from the sample; and a pump system for pumping the liquid sample through the capillary; wherein the pump system is configured such that the rate at which the liquid sample is delivered to the sample receiving surface is equal to the average rate at which the liquid sample is ejected from the sample surface by nebulisation.

2. The nebulisation device of claim 1, further comprising a fluid injection system for injecting a fluid into the liquid sample downstream of the sample separation device for increasing the flow rate out of the capillary outlet.

3. The nebulisation device of claim 1, wherein an exit orifice of the capillary is arranged at a distance from said sample receiving surface such that the liquid sample deposited on the sample receiving surface by the capillary remains in contact with the exit end of the capillary to form a liquid junction between the end of the capillary and the sample receiving surface; and/or wherein the spacing between the exit orifice of the capillary and the sample receiving surface is selected such that the sample receiving surface does not contact and/or seal the exit orifice of the capillary whilst the sample receiving surface is oscillated by the ultrasonic transducer.

4. The nebulisation device of claim 1, wherein the exit orifice of the capillary is spaced apart from the sample receiving surface, and wherein the nebulisation device comprises a pump for pumping the liquid sample through the capillary at a rate such that a column or jet of liquid sample is ejected from the capillary and continuously provided to the sample surface.

5. The nebulisation device of claim 1, comprising a control system for varying the frequency at which the ultrasonic transducer oscillates the sample receiving surface; and wherein the control system is linked to the pump system such that at any given frequency of oscillation for the surface, the rate at which the liquid sample is delivered to the sample receiving surface is maintained equal to the average rate at which liquid sample is ejected from the sample surface by nebulisation.

6. The nebulisation device of claim 1, wherein the sample receiving surface is a substantially planar surface and the planar surface is arranged at an angle to a longitudinal axis through the exit orifice of the capillary and/or at an angle to a longitudinal axis of the capillary.

7. The nebulisation device of claim 6, wherein the angle between the longitudinal axis and the sample receiving surface is ≤$\alpha$ degrees, wherein $\alpha$ is selected from the group consisting of: 40; 35; 30; 25; 20; 15; 10; and 5.

8. The nebulisation device of claim 1, wherein the ultrasonic transducer is coupled to the sample receiving surface such that the sample receiving surface is oscillated back and forth along an oscillation axis; wherein the oscillation axis is at an angle to the plane of the sample receiving surface for ejecting the sample droplets or ions away from the sample receiving surface with a velocity component along said oscillation axis and/or with a velocity component perpendicular to said oscillation axis.

9. The nebulisation device of claim 1, wherein the sample receiving surface is the longitudinal end of an elongated element that is mechanically coupled to the transducer.

10. The nebulisation device of claim 1, wherein said nebuliser is configured such that the cross-sectional area through which the fluid may flow at the exit end of the capillary is adjustable, and wherein the nebulisation device comprises a control device for adjusting said cross-sectional area.

11. A mass or ion mobility spectrometer comprising:

a nebulisation device as claimed in claim 1;

a vacuum chamber; and an ion inlet orifice arranged between the sample receiving surface of the nebulisation device and the vacuum chamber for receiving said ions and/or charged droplets.

12. The spectrometer of claim 11, wherein the nebulisation device is configured such that the transducer oscillates the sample receiving surface such that said charged droplets and/or ions are nebulised from the surface with a velocity component towards the ion inlet orifice; and/or wherein the nebulisation device is configured such that the transducer oscillates the sample receiving surface along an oscillation axis, and wherein the oscillation axis is at an angle to, or perpendicular to, an axis through the ion inlet orifice; and/or wherein the sample receiving surface at least partially faces towards the ion inlet orifice.

13. The spectrometer of claim 11, wherein the ion inlet orifice is located a distance x from a part of the sample receiving surface on which the sample is deposited in use, wherein the distance x is selected from the group consisting of: ≤30 mm; ≤25 mm; ≤20 mm; ≤19 mm; ≤18 mm; ≤17 mm; ≤16 mm; ≤15 mm; ≤14 mm; ≤13 mm; ≤12 mm; ≤11 mm; ≤10 mm; ≤9 mm; ≤8 mm; ≤7 mm; ≤6 mm; and ≤5 mm.

14. The spectrometer of claim 11, wherein the spectrometer is configured to maintain the vacuum chamber at a lower pressure than a nebulising region in which the sample receiving surface is located so as to provide a gas flow from said nebulising region through the ion inlet orifice for drawing the ions and/or charged droplets through the ion inlet orifice.

15. The spectrometer of claim 11, comprising a heater for heating a structural component downstream of the sample receiving surface for heating the nebulised droplets and/or ions.

16. A method of nebulising a liquid sample using a secondary ultrasonic nebulisation device comprising:
delivering a liquid sample from a liquid chromatography separation device to a sample receiving surface; and
ultrasonically oscillating the surface so as to nebulise the liquid sample, wherein said ultrasonically oscillating causes charged droplets and/or gas phase ions to be generated from the sample;
wherein the liquid sample is delivered to the sample receiving surface such that the rate at which the liquid sample is delivered to the sample receiving surface is equal to the average rate at which the liquid sample is ejected from the sample surface by nebulisation.

17. The method of claim 16, comprising adding volatile additives into the liquid sample for assisting ionisation of analyte in the liquid sample during or after nebulisation at the sample receiving surface.

18. The method of claim 17, wherein the additives are activated so as to assist in said ionisation by ultrasonically oscillating the sample receiving surface; and/or wherein the additives are activated so as to assist in said ionisation by variations in pressure caused by ultrasonically oscillating the sample receiving surface.

19. A method of mass spectrometry or ion mobility spectrometry comprising:
a method of nebulising a liquid sample as claimed in claim 16; and
mass analysing or ion mobility analysing said gas phase ions, ions derived from said gas phase ions, or ions derived from said charged droplets.

* * * * *